US011975327B2

(12) United States Patent
Smith et al.

(10) Patent No.: US 11,975,327 B2
(45) Date of Patent: May 7, 2024

(54) INTEGRATED CONTAINER ADAPTER FOR PHOTOACOUSTIC MICROSCOPY

(71) Applicants: Barbara S. Smith, Scottsdale, AZ (US); Christopher Miranda, Tempe, AZ (US); Ethan B. Marschall, Queen Creek, AZ (US)

(72) Inventors: Barbara S. Smith, Scottsdale, AZ (US); Christopher Miranda, Tempe, AZ (US); Ethan B. Marschall, Queen Creek, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 400 days.

(21) Appl. No.: 16/902,110

(22) Filed: Jun. 15, 2020

(65) Prior Publication Data

US 2020/0398268 A1 Dec. 24, 2020

Related U.S. Application Data

(60) Provisional application No. 62/863,658, filed on Jun. 19, 2019.

(51) Int. Cl.
*B01L 3/00* (2006.01)
*G01N 21/17* (2006.01)

(52) U.S. Cl.
CPC .......... *B01L 3/508* (2013.01); *G01N 21/1702* (2013.01); *G01N 2021/1706* (2013.01)

(58) Field of Classification Search
CPC .............. B01L 3/508; B01L 2300/042; B01L 2300/046; B01L 2300/0609;
(Continued)

(56) References Cited

U.S. PATENT DOCUMENTS

| 4,267,732 A | 5/1981 | Quate |
| 5,752,518 A | 5/1998 | Mcgee et al. |

(Continued)

FOREIGN PATENT DOCUMENTS

| CN | 2061692 U | 9/1990 | |
| FR | 2997502 A1 * | 5/2014 | ............ C12M 23/10 |

(Continued)

OTHER PUBLICATIONS

Abbas, J. J.; Smith, B.; Poluta, M.; Velazquez-Berumen, A., Improving health-care delivery in lowresource settings with nanotechnology: Challenges in multiple dimensions. Nanobiomedicine 2017, 4, 1849543517701158.

(Continued)

*Primary Examiner* — Thien M Le
*Assistant Examiner* — Tae W Kim
(74) *Attorney, Agent, or Firm* — Michael Best & Friedrich LLP

(57) ABSTRACT

An adapter for a container that provides an integrated photoacoustic microscopy system that is capable of real time imaging of samples within the container. The adapter allows a researcher or investigator to evaluate a sample using the photoacoustic effect, with or without a microscope. The adapter comprises a support portion, a planar portion, and a tube. The support portion includes a channel formed therein, the channel including a first surface, a second surface opposite the first surface, and an intermediate surface positioned between the first surface and the second surface, the channel configured to receive the rim of the container such that the intermediate surface of the channel is positioned adjacent a top surface of the rim and the first surface and the second surface extend along opposite sides of the sidewall. The planar portion is coupled to the support portion and extends across the opening of the container. The tube is (Continued)

coupled to and extends from the planar portion, the tube defines a bore having an axis, the axis being oriented at an angle relative to the planar portion, the bore configured to receive a photoacoustic transducer for real time imaging of a sample within the container.

18 Claims, 3 Drawing Sheets

(58) Field of Classification Search
CPC ........ B01L 2300/0654; G01N 21/1702; G01N 2021/1706; C12M 23/38; C12M 41/36; C12M 23/10
USPC .......................................................... 73/24
See application file for complete search history.

(56) References Cited

U.S. PATENT DOCUMENTS

| | | | |
|---|---|---|---|
| 8,932,223 | B2 | 1/2015 | Emelianov et al. |
| 9,618,445 | B2 | 4/2017 | Sun et al. |
| 10,107,613 | B2 | 10/2018 | Jiao et al. |
| 10,795,440 | B1 | 10/2020 | Chevillet et al. |
| 2007/0299341 | A1 | 12/2007 | Wang et al. |
| 2010/0079580 | A1 | 4/2010 | Waring, IV |
| 2010/0245766 | A1 | 9/2010 | Zhang et al. |
| 2011/0098530 | A1 | 4/2011 | Yamane |
| 2011/0282192 | A1 | 11/2011 | Axelrod et al. |
| 2011/0301458 | A1 | 12/2011 | Li et al. |
| 2012/0275262 | A1 | 11/2012 | Song et al. |
| 2013/0158383 | A1 | 6/2013 | Cheng et al. |
| 2013/0216114 | A1 | 8/2013 | Courtney et al. |
| 2014/0066743 | A1 | 3/2014 | Nakajima et al. |
| 2014/0142404 | A1 | 5/2014 | Wang et al. |
| 2015/0160168 | A1 | 6/2015 | Irisawa |
| 2015/0226845 | A1 | 8/2015 | Witte et al. |
| 2015/0247999 | A1 | 9/2015 | Ntziachristos et al. |
| 2015/0327768 | A1 | 11/2015 | Oyama et al. |
| 2016/0003777 | A1 | 1/2016 | Schmitt-Manderbach et al. |
| 2016/0143542 | A1 | 5/2016 | Bossy et al. |
| 2016/0242651 | A1 | 8/2016 | Wang et al. |
| 2016/0249812 | A1 | 9/2016 | Wang et al. |
| 2016/0250073 | A1 | 9/2016 | Gooding et al. |
| 2016/0305914 | A1 | 10/2016 | Wang et al. |
| 2016/0356746 | A1 | 12/2016 | Piestun et al. |
| 2017/0055841 | A1 | 3/2017 | Mueller et al. |
| 2017/0065182 | A1 | 3/2017 | Wang et al. |
| 2017/0105626 | A1 | 4/2017 | Yisawa |
| 2017/0156600 | A1 | 6/2017 | Ntziachristos et al. |
| 2017/0367682 | A1 | 12/2017 | Smith et al. |
| 2018/0055343 | A1 | 3/2018 | Yang et al. |
| 2018/0078143 | A1 | 3/2018 | Pramanik et al. |
| 2018/0132728 | A1 | 5/2018 | Wang et al. |
| 2018/0214119 | A1 | 8/2018 | Mehrmohammadi et al. |
| 2018/0235570 | A1 | 8/2018 | Fukushima |
| 2019/0046159 | A1 | 2/2019 | Smith et al. |
| 2019/0094208 | A1* | 3/2019 | Vuong ................... C12M 21/08 |
| 2019/0110691 | A1 | 4/2019 | Smith et al. |
| 2019/0175938 | A1 | 6/2019 | Rezaie et al. |
| 2019/0227038 | A1 | 7/2019 | Wang et al. |
| 2019/0282069 | A1 | 9/2019 | Smith et al. |
| 2020/0056986 | A1 | 2/2020 | Wang et al. |
| 2020/0160522 | A1* | 5/2020 | Merlo ....................... B01L 9/52 |
| 2020/0173965 | A1 | 6/2020 | Sangu |
| 2020/0340954 | A1 | 10/2020 | Smith et al. |
| 2021/0080708 | A1 | 3/2021 | Sangu |
| 2022/0151496 | A1 | 5/2022 | Waldner et al. |

FOREIGN PATENT DOCUMENTS

| | | | | |
|---|---|---|---|---|
| IN | | 308501 B | 4/2019 | |
| WO | WO2008075299 | A1 | 6/2008 | |
| WO | WO2008100386 | A2 | 8/2008 | |
| WO | WO-2009050632 | A1 * | 4/2009 | .......... A61B 5/0059 |
| WO | WO2015175431 | A1 | 11/2015 | |
| WO | WO-2015183092 | A1 * | 12/2015 | ............. C12M 23/10 |

OTHER PUBLICATIONS

Abe, Y.-W. Shi, Y. Matsuura, and M. Miyagi, "Flexible small-bore hollow fibers with an inner polymer coating," Opt. letters 25, 150-152 (2000).

Addington, CP, Dharmaraj, S, Heffernan, JM, Sirianni, RW, Stabenfeldt, SE. Hyaluronic acid- laminin hydrogels increase neural stem cell transplant retention and migratory response to SDF-1α. Matrix Biology. 2017, 60-61, 206-216.

Anand, S.; Kumar, S. S.; Muthuswamy, J., Autonomous control for mechanically stable navigation of microscale implants in brain tissue to record neural activity. Biomedical Microdevices 2016, 18 (4).

Anderson, T. R.; Hu, B.; Iremonger, K.; Kiss, Z. H. T., Selective attenuation of afferent synaptic transmission as a mechanism of thalamic deep brain stimulation-induced tremor arrest. Journal of Neuroscience 2006, 26 (3), 841-850.

Anderson, T. R.; Huguenard, J. R.; Prince, D. A., Differential effects of Na plus -K plus ATPase blockade on cortical layer V neurons. Journal of Physiology-London 2010, 588 (22), 4401-4414.

Andrasfalvy, B. K.; Galinanes, G. L.; Huber, D.; Barbic, M.; Macklin, J. J.; Susumu, K.; Delehanty, J. B.; Huston, A. L.; Makara, J. K.; Medintz, I. L., Quantum dot-based multiphoton fluorescent pipettes for targeted neuronal electrophysiology. Nat. Methods 2014, 11 (12), 1237-1241.

Annecchino, A. R. Morris, C. S. Copeland, O. E. Agabi, P. Chadderton, and S. R. Schultz, "Robotic automation of in vivo two-photon targeted whole-cell patch-clamp electrophysiology," Neuron 95, 1048-1055 (2017).

Aravanis, A. M.; Wang, L. P.; Zhang, F.; Meltzer, L. A.; Mogri, M. Z.; Schneider, M. B.; Deisseroth, K., An optical neural interface: in vivo control of rodent motor cortex with integrated fiberoptic and optogenetic technology. Journal of Neural Engineering 2007, 4 (3), S143-S156.

Aston-Jones, G.; Deisseroth, K., Recent advances in optogenetics and pharmacogenetics. Brain Research 2013, 1511, 1-5.

Badu-Tawiah, A. K.; Lathwal, S.; Kaastrup, K.; Al-Sayah, M.; Christodouleas, D. C.; Smith, B. S.; Whitesides, G. M.; Sikes, H. D., Polymerization-based signal amplification for paper-based immunoassays. Lab on a chip 2015, 15 (3), 655-659.

Balaic, D. X.; Nugent, K. A., x-ray optics of tapered capillaries. Applied Optics 1995, 34 (31), 7263-7272.

Beard, P., Biomedical photoacoustic imaging. Interface Focus 2011, 1 (4), 602-631.

Beaulieu-Laroche, L .; Harnett, M. T., Dendritic Spines Prevent Synaptic Voltage Clamp. Neuron 2018, 97 (1), 75-82.

Bilderback, D. H.; Fontes, E., Glass capillary optics for making x-ray beams of 0.1 to 50 microns diameter. AIP Conference Proceedings 1997, Medium: X; Size: pp. 147-155.

Billet, A.; Froux, L.; Hanrahan, J. W.; Becq, F., Development of Automated Patch Clamp Technique to Investigate CFTR Chloride Channel Function. Frontiers in Pharmacology 2017, 8.

Bohndiek, S. Bodapati, D. Van De Sompel, S.-R. Kothapalli, and S. S. Gambhir, "Development and application of stable phantoms for the evaluation of photoacoustic imaging instruments," PloS one 8, e75533 (2013).

Bornstein, J. C.; Furness, J. B., correlated electrophysiological and histochemical-studies of submucous neurons and their contribution to understanding enteric neural circuits. Journal of the Autonomic Nervous System 1988, 25 (1), 1-13.

Boyden, E. S.; Zhang, F.; Bamberg, E.; Nagel, G.; Deisseroth, K., Millisecond-timescale, genetically targeted optical control of neural activity. Nature Neuroscience 2005, 8 (9), 1263-1268.

Chen, C. C.; Cang, C. L.; Fenske, S.; Butz, E.; Chao, Y. K.; Biel, M.; Ren, D. J.; Wahl-Schott, C.; Grimm, C., Patch-clamp technique to characterize ion channels in enlarged individual endolysosomes. Nat. Protoc. 2017, 12 (8), 1639-1658.

(56) References Cited

OTHER PUBLICATIONS

Cox, B.; Laufer, J. G.; Arridge, S. R.; Beard, P. C., Quantitative spectroscopic photoacoustic imaging: a review. J. Biomed. Opt. 2012, 17 (6).
Cullen, D. K.; Stabenfeldt, S. E.; Simon, C. M.; Tate, C. C.; LaPlaca, M. C., In vitro neural injury model for optimization of tissue-engineered constructs. Journal of Neuroscience Research 2007, 85 (16), 3642-3651.
De La Zerda, Adam, et al. "Carbon nanotubes as photoacoustic molecular imaging agents in living mice." Nature nanotechnology 3.9 (2008): 557.
Deisseroth, K., Optogenetics. Nat. Methods 2011, 8 (1), 26-29.
Desai, N. S.; Siegel, J. J.; Taylor, W.; Chitwood, R. A.; Johnston, D., MATLAB-based automated patch-clamp system for awake behaving mice. Journal of Neurophysiology 2015, 114 (2), 1331-1345.
Dika et al., Early experiences and integration in the persistence of first-generation college students in STEM and non-STEM majors. Journal of Research in Science Teaching 2016, 53 (3), 368-383.
Dunn, R. C., Near-field scanning optical microscopy. Chemical reviews 1999, 99 (10), 2891-2928.
Fan, B.; Li, W., Miniaturized optogenetic neural implants: a review. Lab on a Chip 2015, 15 (19), 3838-3855.
Fenno, L.; Yizhar, O.; Deisseroth, K., The Development and Application of Optogenetics. In Annual Review of Neuroscience, vol. 34, Hyman, S. E.; Jessell, T. M.; Shatz, C. J.; Stevens, C. F.; Zoghbi, H. Y., Eds. 2011; vol. 34, pp. 389-412.
Frow, E. K.; Smith, B. S .; Ankeny, C. J. In Freshman design course: Device design for low- resource settings, ASEE Annual Conference and Exposition, Conference Proceedings, 2017.
Galanzha, E. I.; Shashkov, E. V.; Spring, P. M.; Suen, J. Y.; Zharov, V. P., In vivo, Noninvasive, Label-Free Detection and Eradication of Circulating Metastatic Melanoma Cells Using Two-Color Photoacoustic Flow Cytometry with a Diode Laser. Cancer Research 2009, 69 (20), 7926-7934.
Goddeyne, C.; Nichols, J.; Wu, C.; Anderson, T., Repetitive mild traumatic brain injury induces ventriculomegaly and cortical thinning in juvenile rats. Journal of Neurophysiology 2015, 113 (9), 3268-3280.
Gooch, C. L.; Pracht, E.; Borenstein, A. R., The burden of neurological disease in the United States: A summary report and call to action. Annals of neurology 2017, 81 (4), 479-484.
Grewe, B. F.; Langer, D.; Kasper, H.; Kampa, B. M.; Helmchen, F., High-speed in vivo calcium imaging reveals neuronal network activity with near-millisecond precision (vol. 7, p. 399, 2010). Nat. Methods 2010, 7 (6), 479-479.
Hamill, O. P.; Marty, A.; Neher, E.; Sakmann, B.; Sigworth, F. J., improved patch-clamp techniques for high-resolution current recording from cells and cell-free membrane patches. Pflugers Arch. 1981, 391 (2), 85-100.
Harvey, C. D.; Collman, F.; Dombeck, D. A.; Tank, D. W., Intracellular dynamics of hippocampal place cells during virtual navigation. Nature 2009, 461 (7266), 941-U196.
Hayar, C. Gu, and E. D. Al-Chaer, "An improved method for patch clamp recording and calcium imaging of neurons in the intact dorsal root ganglion in rats," J. neuroscience methods 173, 74-82 (2008).
Hecht, B.; Sick, B.; Wild, U. P.; Deckert, V.; Zenobi, R.; Martin, O. J. F.; Pohl, D. W., Scanning near-field optical microscopy with aperture probes: Fundamentals and applications. Journal of Chemical Physics 2000, 112 (18), 7761-7774.
Helmchen, F.; Denk, W., Deep tissue two-photon microscopy. Nat. Methods 2005, 2 (12), 932-940.
Hu, S.; Maslov, K.; Wang, L. V., Second-generation optical-resolution photoacoustic microscopy with improved sensitivity and speed. Opt. Lett. 2011, 36 (7), 1134-1136.
Hurtado, S.; Newman, C. B.; Tran, M. C.; Chang, M. J., Improving the Rate of Success for Underrepresented Racial Minorities in STEM Fields: Insights from a National Project. New Directions for Institutional Research 2010, 148, 5-15.
Ishitani, T. T., Studying attrition and degree completion behavior among first-generation college students in the United States. The Journal of Higher Education 2006, 77 (5), 861-885.
Jansen, M. Wu, A. F. van der Steen, and G. van Soest, "Lipid detection in atherosclerotic human coronaries by spectroscopic intravascular photoacoustic imaging," Opt. express 21, 21472-21484 (2013).
Karpiouk, B. Wang, J. Amirian, R. W. Smalling, and S. Y. Emelianov, "Feasibility of in vivo intravascular photoacoustic imaging using integrated ultrasound and photoacoustic imaging catheter," J. biomedical optics 17, 0960081-0960086 (2012).
Keene, A. C.; Waddell, S., Drosophila olfactory memory: single genes to complex neural circuits. Nature Reviews Neuroscience 2007, 8 (5), 341-354.
Khraiche, W Phillips*, N Jackson*, J Muthuswamy, "Sustained Elevation of Activity of Developing Neurons Grown on Polyamide Microelectrode Arrays (MEA) in Response to Ultrasound Exposure," Microsystem Technologies, 2017, 23:3671-3683.
Kim, E. Chung, H. Yamashita, K. E. Hung, A. Mizoguchi, R. Kucherlapati, D. Fukumura, R. K. Jain, and S. H. Yun, "In vivo wide-area cellular imaging by side-view endomicroscopy," Nat. methods 7, 303 (2010).
Kim, Taeho et al. "Photoacoustic Imaging of Human Mesenchymal Stem Cells Labeled with Prussian Blue-Poly(l-lysine) Nanocomplexes." ACS nano vol. 11,9 (2017): 9022-9032. doi:10.1021/acsnano. 7b03519.
Kitamura, B. Judkewitz, M. Kano, W. Denk, and M. Häusser, "Targeted patch-clamp recordings and single-cell electroporation of unla-beled neurons in vivo," Nat. methods 5, 61-67 (2008).
Kodandaramaiah, G. L. Holst, I. R. Wickersham, A. C. Singer, G. T. Franzesi, M. L. McKinnon, C. R. Forest, and E. S. Boyden, "Assembly and operation of the autopatcher for automated intracellular neural recording in vivo," Nat. protocols 11, 634-654 (2016).
Kodandaramaiah, S. B.; Boyden, E. S.; Forest, C. R.; New York Acad, S., In vivo robotics: the automation of neuroscience and other intact-system biological fields. In Conference Reports: Evolutionary Dynamics and Information Hierarchies in Biological Systems: Aspen Center for Physics Workshop and Cracking the Neural Code: Third Annual Aspen Brain Forums, Blackwell Science Publ: Oxford, 2013; vol. 1305, pp. 63-71.
Kodandaramaiah, S. B.; Franzesi, G. T.; Chow, B. Y.; Boyden, E. S.; Forest, C. R., Automated whole-cell patch-clamp electrophysiology of neurons in vivo. Nat. Methods 2012, 9 (6), 585-+.
Kodandaramaish, S. B.; Flores, F. J.; Holst, G. L.; Singer, A. C.; Han, X.; Brown, E. N.; Boyden, E. S.; Forest, C. R., Multi-neuron intracellular recording in vivo via interacting autopatching robots. eLife 2018, 7, 19.
Kozodoy, A. T. Pagkalinawan, and J. A. Harrington, "Small-bore hollow waveguides for delivery of 3-mm laser radiation," Appl. optics 35, 1077-1082 (1996).
Ku, G.; Wang, X. D.; Xie, X. Y.; Stoica, G.; Wang, L. H. V., Imaging of tumor angiogenesis in rat brains in vivo by photoacoustic tomography. Applied Optics 2005, 44 (5), 770-775.
Kumar et al., From the Bench to the Field in Low-Cost Diagnostics: Two Case Studies. Angewandte Chemie International Edition 2015, 54 (20), 5836-5853.
LeChasseur, Y.; Dufour, S.; Lavertu, G.; Bories, C.; Deschenes, M.; Vallee, R.; De Koninck, Y., A microprobe for parallel optical and electrical recordings from single neurons in vivo. Nat. Methods 2011, 8 (4), 319-U63.
Llinas, R. R., Intrinsic electrical properties of mammalian neurons and CNS function: a historical perspective. Frontiers in Cellular Neuroscience 2014, 8.
Long, L. Li, U. Knoblich, H. Zeng, and H. Peng, "3d image-guided automatic pipette positioning for single cell experiments in vivo," Sci. reports 5, 18426 (2015).
Long, M. A.; Jin, D. Z. Z.; Fee, M. S., Support for a synaptic chain model of neuronal sequence generation. Nature 2010, 468 (7322), 394-399.
Lu, W.; Huang, Q.; Geng, K. B.; Wen, X. X.; Zhou, M.; Guzatov, D.; Brecht, P.; Su, R.; Oraevsky, A.; Wang, L. V.; Li, C., Photoacoustic imaging of living mouse brain vasculature using hollow gold nanospheres. Biomaterials 2010, 31 (9), 2617-2626.

(56) References Cited

OTHER PUBLICATIONS

Lusk, Joel F., et al. "Photoacoustic Flow System for the Detection of Ovarian Circulating Tumor Cells Utilizing Copper Sulfide Nanoparticles." ACS Biomaterials Science & Engineering (2019).
Mallidi, S.; Luke, G. P.; Emelianov, S., Photoacoustic imaging in cancer detection, diagnosis, and treatment guidance. Trends in Biotechnology 2011, 29 (5), 213-221.
Margrie, A. H. Meyer, A. Caputi, H. Monyer, M. T. Hasan, A. T. Schaefer, W. Denk, and M. Brecht, "Targeted whole-cell recordings in the mammalian brain in vivo," Neuron 39, 911-918 (2003).
Markram, H.; Lubke, J.; Frotscher, M.; Roth, A.; Sakmann, B., Physiology and anatomy of synaptic connections between thick tufted pyramidal neurones in the developing rat neocortex. Journal of Physiology-London 1997, 500 (2), 409-440.
Maslov, K.; Zhang, H. F.; Hu, S.; Wang, L. V., Optical-resolution photoacoustic microscopy for in vivo imaging of single capillaries. Opt. Lett. 2008, 33 (9), 929-931.
Matsuura, T. Abel, and J. A. Harrington, "Optical properties of smallbore hollow glass waveguides," Appl. optics 34, 6842-6847 (1995).
Matsuura, T. Abel, J. Hirsch, and J. Harrington, "Small-bore hollow waveguide for delivery of near singlemode ir laser radiation," Electron. Lett. 30, 1688-1690 (1994).
Miranda et al., "Side-viewing Photoacoustic Capillary Endoscope," 2018, Optics Letters, 1-4.
Miranda, C.; Barkley, J.; Smith, B. S., Intrauterine photoacoustic and ultrasound imaging probe. J. Biomed. Opt. 2018, 23 (4), 9.
Miranda, Christopher, et al. "Photoacoustic micropipette." Applied Physics Letters 113.26 (2018): 264103.
Neher, E.; Sakmann, B., single-channel currents recorded from membrane of denervated frog muscle-fibers. Nature 1976, 260 (5554), 799-802.
Nichols, J.; Bjorklund, G. R.; Newbern, J.; Anderson, T., Parvalbumin fast-spiking interneurons are selectively altered by paediatric traumatic brain injury. Journal of Physiology-London 2018, 596(7), 1277-1293.
Nichols, J.; Perez, R.; Wu, C.; Adelson, P. D.; Anderson, T., Traumatic Brain Injury Induces Rapid Enhancement of Cortical Excitability in Juvenile Rats. Cns Neuroscience & Therapeutics 2015, 21 (2), 193-203.
Olsen, S. R.; Wilson, R. I., Cracking neural circuits in a tiny brain: new approaches for understanding the neural circuitry of Drosophila. Trends in Neurosciences 2008, 31 (10), 512- 520.
Ovsepian, Saak V., et al. "Pushing the boundaries of neuroimaging with optoacoustics." Neuron 96.5 (2017): 966-988.
Papadopoulos, O. Simandoux, S. Farahi, J. Pierre Huignard, E. Bossy, D. Psaltis, and C. Moser, "Optical-resolution photoacoustic microscopy by use of a multimode fiber," Appl. Phys. Lett. 102, 211106 (2013).
Papadopoulos, S. Farahi, C. Moser, and D. Psaltis, "Highresolution, lensless endoscope based on digital scanning through a multimode optical fiber," Biomed. optics express 4, 260-270 (2013).
Patil, Ujwal, et al. "In vitro/in vivo toxicity evaluation and quantification of iron oxide nanoparticles." International journal of molecular sciences 16.10 (2015): 24417-24450.
Pisanello, F.; Sileo, L.; Oldenburg, I. A.; Pisanello, M.; Martiradonna, L.; Assad, J. A.; Sabatini, B.L.; De Vittorio, M., Multipoint-Emitting Optical Fibers for Spatially Addressable In Vivo Optogenetics. Neuron 2014, 82 (6), 1245-1254.
Richter, D. W.; Pierrefiche, O.; Lalley, P. M.; Polder, H. R., Voltage-clamp analysis of neurons within deep layers of the brain. J. Neurosci. Methods 1996, 67 (2), 121-131.
Rose, G. J.; Alluri, R. K.; Vasquez-Opazo, G. A.; Odom, S. E.; Graham, J. A.; Leary, C. J., Combining pharmacology and whole-cell patch recording from CNS neurons, in vivo. J. Neurosci. Methods 2013, 213 (1), 99-104.
Saiki, T.; Matsuda, K., Near-field optical fiber probe optimized for illumination-collection hybrid mode operation. Applied Physics Letters 1999, 74 (19), 2773-2775.
Schneider, D. M.; Nelson, A.; Mooney, R., A synaptic and circuit basis for corollary discharge in the auditory cortex. Nature 2014, 513 (7517), 189-+.
Sethuraman, S. R. Aglyamov, J. H. Amirian, R. W. Smalling, and S. Y. Emelianov, "Intravascular photoacoustic imaging using an ivus imaging catheter," IEEE transactions on ultrasonics, ferroelectrics, frequency control 54 (2007).
Shi, K. Ito, L. Ma, T. Yoshida, Y. Matsuura, and M. Miyagi, "Fabrication of a polymer-coated silver hollow optical fiber with high performance," Appl. optics 45, 6736-6740 (2006).
Shung, J. Cannata, and Q. Zhou, "Piezoelectric materials for high frequency medical imaging applications: A review," J. Electroceramics 19, 141-147 (2007).
Simandoux, N. Stasio, J. Gateau, J.-P. Huignard, C. Moser, D. Psaltis, and E. Bossy, "Optical-resolution photoacoustic imaging through thick tissue with a thin capillary as a dual optical-in acousticout waveguide," Appl. Phys. Lett. 106, 094102 (2015).
Smetters, D.; Majewska, A.; Yuste, R., Detecting action potentials in neuronal populations with calcium imaging. Methods-a Companion to Methods in Enzymology 1999, 18 (2), 215-221.
Smith, A Shah, Yong-Kyun Lee, B O'Brien, D Kullman, A Sridharan, J Muthuswamy, J B Christen "Optogenetic Neurostimulation of the Auricular Vagus using Flexible OLED Display Technology to Treat Chronic Inflammatory Disease and Mental Health Disorders" Electronics Letters, DOI: 10.1049/el.2015.3450, 2016.
So, P. T. C.; Dong, C. Y.; Masters, B. R.; Berland, K. M., Two-photon excitation fluorescence microscopy. Annual Review of Biomedical Engineering 2000, 2, 399-429.
Stasio, A. Shibukawa, I. N. Papadopoulos, S. Farahi, O. Simandoux, J.-P. Huignard, E. Bossy, C. Moser, and D. Psaltis, "Towards new applications using capillary waveguides," Biomed. optics express 6, 4619-4631 (2015).
Stern, E. A.; Kalman, Z.; Lewis, A.; Lieberman, K., simple method for focusing x-rays using tapered capillaries. Applied Optics 1988, 27 (24), 5135-5139.
Stosiek, C.; Garaschuk, O.; Holthoff, K.; Konnerth, A., In vivo two-photon calcium imaging of neuronal networks. Proc. Natl. Acad. Sci. U. S. A. 2003, 100 (12), 7319-7324.
Strohm, E. M.; Moore, M. J.; Kolios, M. C., Single Cell Photoacoustic Microscopy: A Review. Ieee Journal of Selected Topics in Quantum Electronics 2016, 22 (3).
Stuart, G. J.; Dodt, H. U.; Sakmann, B., patch-clamp recordings from the soma and dendrites of neurons in brain-slices using infrared video microscopy. Pflugers Arch. 1993, 423 (5-6), 511-518.
Suk, I. van Welie, S. B. Kodandaramaiah, B. Allen, C. R. Forest, and E. S. Boyden, "Closed-loop real-time imaging enables fully automated cell-targeted patch-clamp neural recording in vivo," Neuron. 95, 1037-1047 (2017).
Svoboda, K.; Yasuda, R., Principles of two-photon excitation microscopy and its applications to neuroscience. Neuron 2006, 50 (6), 823-839.
Timofeev, I.; Grenier, F.; Steriade, M., Disfacilitation and active inhibition in the neocortex during the natural sleep-wake cycle: An intracellular study. Proc. Natl. Acad. Sci. U. S. A. 2001, 98 (4), 1924-1929.
Vasilyev, D.; Merrill, T.; Iwanow, A.; Dunlop, J.; Bowlby, M., A novel method for patch-clamp automation. Pflugers Arch. 2006, 452 (2), 240-247.
Veerman, J. A.; Otter, A. M.; Kuipers, L.; van Hulst, N. F., High definition aperture probes for nearfield optical microscopy fabricated by focused ion beam milling. Applied Physics Letters 1998, 72 (24), 3115-3117.
Wang and S. Hu, "Photoacoustic tomography: in vivo imaging from organelles to organs," Science 335, 1458-1462 (2012).
Wang, A. Karpiouk, D. Yeager, J. Amirian, S. Litovsky, R. Smalling, and S. Emelianov, "Intravascular photoacoustic imaging of lipid in atherosclerotic plaques in the presence of luminal blood," Opt. letters 37, 1244-1246 (2012).
Wang, C.- C.; Hennek, J. W.; Ainla, A.; Kumar, A. A.; Lan, W.- J.; Im, J.; Smith, B. S.; Zhao, M.; Whitesides, G. M., A Paper-Based "Pop-up" Electrochemical Device for Analysis of Beta-Hydroxybutyrate. Analytical Chemistry 2016, 88 (12), 6326-6333.

(56) References Cited

OTHER PUBLICATIONS

Wang, J. L. Su, A. B. Karpiouk, K. V. Sokolov, R. W. Smalling, and S. Y. Emelianov, "Intravascular photoacoustic imaging," IEEE J. selected topics Quantum Electron. 16, 588-599 (2010).
Wang, L. V., Multiscale photoacoustic microscopy and computed tomography. Nature Photonics 2009, 3 (9), 503-509.
Wang, T. Ma, M. N. Slipchenko, S. Liang, J. Hui, K. K. Shung, S. Roy, M. Sturek, Q. Zhou, Z. Chen, and J.-X. Cheng, "High-speed intravascular photoacoustic imaging of lipid-laden atherosclerotic plaque enabled by a 2-khz barium nitrite raman laser," Sci. reports 4, 6889 (2014).
Wang, X. D.; Pang, Y. J.; Ku, G.; Xie, X. Y.; Stoica, G.; Wang, L. H. V., Noninvasive laser-induced photoacoustic tomography for structural and functional in vivo imaging of the brain. Nat. Biotechnol. 2003, 21 (7), 803-806.
Wang, X. D.; Xie, X. Y.; Ku, G. N.; Wang, L. H. V., Noninvasive imaging of hemoglobin concentration and oxygenation in the rat brain using high-resolution photoacoustic tomography. J. Biomed. Opt. 2006, 11 (2).
Weber, Judith, Paul C. Beard, and Sarah E. Bohndiek. "Contrast agents for molecular photoacoustic imaging." Nature methods 13.8 (2016): 639.
Wong, Terence TW, et al. "Fast label-free multilayered histology-like imaging of human breast cancer by photoacoustic microscopy." Science advances 3.5 (2017): e1602168.
Wu, I. Kolb, B. M. Callahan, Z. Su, W. Stoy, S. B. Kodandaramaiah, R. Neve, H. Zeng, E. S. Boyden, C. R. Forest, and A. A. Chubykin, "Integration of autopatching with automated pipette and cell detection in vitro," J. neurophysiology 116, 1564-1578 (2016).
Xu, Minghua, and Lihong V. Wang. "Photoacoustic imaging in biomedicine." Review of scientific instruments 77.4 (2006): 041101.
Yajuan, X .; Xin, L .; Zhiyuan, L., A comparison of the performance and application differences between manual and automated patch-clamp techniques. Curr Chem Genomics 2012, 6, 87-92.
Yang, C. Favazza, J. Yao, R. Chen, Q. Zhou, K. K. Shung, and L. V. Wang, "Three-dimensional photoacoustic endoscopic imaging of the rabbit esophagus," PloS one 10, e0120269 (2015).
Yang, C. Favazza, R. Chen, J. Yao, X. Cai, K. Maslov, Q. Zhou, K. K. Shung, and L. V. Wang, "Simultaneous functional photoacoustic and ultrasonic endoscopy of internal organs in vivo," Nat. medicine 18, 1297-1302 (2012).
Yang, C. Favazza, R. Chen, K. Maslov, X. Cai, Q. Zhou, K. K. Shung, and L. V. Wang, "Volumetric photoacoustic endoscopy of upper gastrointestinal tract: ultrasonic transducer technology development," in Proc. SPIE, , vol. 7899 (2011), pp. 78990D1-78990D6.
Yang, K. Maslov, H.-C. Yang, Q. Zhou, K. K. Shung, and L. V. Wang, "Photoacoustic endoscopy," Opt. letters 34, 1591-1593 (2009).
Yang, R.; Lai, K. W. C.; Xi, N.; Yang, J., Development of automated patch clamp system for electrophysiology. In 2013 IEEE International Conference on Robotics and Biomimetics, ROBIO 2013, 2013; p. 2185.
Yang, R.; Tam, C. H.; Cheung, K. L.; Wong, K. C.; Xi, N.; Yang, J.; Lai, W. C. K., Cell Segmentation and Pipette Identification for Automated Patch Clamp Recording. Robotics and Biomimetics 2014, 1 (20), 1-12.
Yao, K. Maslov, K. K. Shung, Q. Zhou, and L. V. Wang, "In vivo label-free photoacoustic microscopy of cell nuclei by excitation of dna and rna," Opt. letters 35, 4139-4141 (2010).
Yizhar, O.; Fenno, L. E.; Davidson, T. J.; Mogri, M.; Deisseroth, K., Optogenetics in Neural Systems. Neuron 2011, 71 (1), 9-34.
Zhang and P. C. Beard, "A miniature all-optical photoacoustic imaging probe," in Proc. SPIE, , vol. 7899 (2011), p. 78991F.
Zhang, C.; Maslov, K.; Wang, L. H. V., Subwavelength-resolution label-free photoacoustic microscopy of optical absorption in vivo. Opt. Lett. 2010, 35 (19), 3195-3197.
Zhang, H. F.; Maslov, K.; Stoica, G.; Wang, L. H. V., Functional photoacoustic microscopy for high-resolution and noninvasive in vivo imaging. Nat. Biotechnol. 2006, 24 (7), 848-851.
Zhang, J. Y.; Laiwalla, F.; Kim, J. A.; Urabe, H.; Van Wagenen, R.; Song, Y. K.; Connors, B. W.; Zhang, F.; Deisseroth, K.; Nurmikko, A. V., Integrated device for optical stimulation and spatiotemporal electrical recording of neural activity in light-sensitized brain tissue. Journal of Neural Engineering 2009, 6 (5).
Zharov, V. P.; Galanzha, E. I.; Shashkov, E. V.; Khlebtsov, N. G.; Tuchin, V. V., In vivo photoacoustic flow cytometry for monitoring of circulating single cancer cells and contrast agents. Opt. Lett. 2006, 31 (24), 3623-3625.
Zharov, V. P.; Galanzha, E. I.; Shashkov, E. V.; Kim, J. W.; Khlebtsov, N. G.; Tuchin, V. V., Photoacoustic flow cytometry: principle and application for real-time detection of circulating single nanoparticles, pathogens, and contrast dyes in vivo. J. Biomed. Opt. 2007, 12 (5).
Knight et al., "Hollow-Core Optical Fibers Offer Advantages at Any Wavelength," Photonics Spectra, Apr. 2019.
U.S. Appl. No. 16/159,167 dated Mar. 23, 2021 (15 pages).
Kuck, N., et al. "Visible electroluminescent subwavelength point source of light." Applied physics letters 61.2 (1992): 139-141.
Thor Labs "Achromatic Pairs" 2011 (Year: 2011) (3 pages).
Freudenrich, C. How Fiber Optics Work. Mar. 6, 2001, HowStuffWorks.com, pp. 1-9 (Year: 2001).

\* cited by examiner

INTEGRATED CONTAINER ADAPTER FOR PHOTOACOUSTIC MICROSCOPY

CROSS-REFERENCE TO RELATED APPLICATIONS

This application is a non-provisional of and claims the benefit of U.S. Provisional Patent Application No. 62/863,658, filed on Jun. 19, 2019, the contents of which are incorporated herein by reference.

BACKGROUND

Optical microscopy is a common tool used in laboratory settings, for use in qualitative and quantitative analysis of a sample (e.g., biologicals, chemicals, or material properties). Petri dishes are used to contain a sample to be analyzed.

The photoacoustic effect is the phenomenon of an acoustic wave being generated as a consequence of electromagnetic wave absorption. When non-ionizing laser pulses are delivered, some energy gets converted to heat, causing the thermoelastic expansion, and then the generation of an ultrasonic wave from the rapid pressure differential. This effect relies on the differential thermoelastic expansion of the tissue, allowing the ability to examine the tissue in what is known as photoacoustic imaging.

Photoacoustic imaging is an imaging modality which derives contrast from the differences in optical absorption of the sample being analyzed, which may result from cellular structure, chemical structure, biologicals and the like, combining the high contrast of optical imaging with the resolution and improved depth of ultrasound. This technique has promise in its ability to differentiate characteristics of living tissue as physiological changes may affect the optical properties of a structure. Some endogenous molecules providing contrast may include DNA, RNA, hemoglobin, water, and lipids. Further contrast is possible through various means, such as dyes or receptor-specific absorbers, with popular examples being fluorescent proteins and nanoparticles.

A typical photoacoustic imaging system is comprised of a pulse-energy source and an acoustic detector—multiple variations of this system exist. This has important and widespread application in areas ranging from cancer detection to brain mapping.

SUMMARY

Disclosed herein is a simple and low cost tool that provides a method of imaging a sample in a petri dish easily and quickly. The tool provides an integrated photoacoustic microscopy system that is capable of real time imaging for samples within a commercially available petri dish, which would allow the researcher or investigator to evaluate a sample using the photoacoustic effect, with or without a microscope.

This novel tool allows for aligned placement of a transducer and an optical fiber or microscope objective adjacent or atop a container of variable size and dimensions. This enables photoacoustic microscopy to be performed at the same time as optical or fluorescence microscopy when the dish is placed on the microscope stage. The transducer can be a single (focused or unfocused) item or an array. Additionally, the optical fiber can be aligned with the objective of the microscope in order to perform electrophysiology on cells or tissue samples. A variety of arrangements can be utilized to enable multimodal imaging and microscopy on biologicals, chemicals or materials for use across a variety of fields.

In one embodiment, the disclosure provides an adapter for a container. The container includes a bottom wall, a rim, a sidewall positioned between the bottom wall and the rim, and an opening defined by the rim. The adapter comprises a support portion, a planar portion, and a tube. The support portion includes a channel formed therein, the channel including a first surface, a second surface opposite the first surface, and an intermediate surface positioned between the first surface and the second surface, the channel configured to receive the rim of the container such that the intermediate surface of the channel is positioned adjacent a top surface of the rim and the first surface and the second surface extend along opposite sides of the sidewall. The planar portion is coupled to the support portion and extends across the opening of the container. The tube is coupled to and extends from the planar portion, the tube defines a bore having an axis, the axis being oriented at an angle relative to the planar portion, the bore configured to receive a photoacoustic transducer for real time imaging of a sample within the container.

In another embodiment, the disclosure provides an adapter for a petri dish. The petri dish includes a bottom wall, a rim, a sidewall positioned between the bottom wall and the rim, and an opening defined by the rim. The adapter comprises an arcuately-shaped support portion including a first side and a second side, and a channel formed within the support portion and extending between the first side and the second side, the channel configured to receive the rim of the petri dish. The adapter also includes a planar portion coupled to the support portion between the first side and the second side, the planar portion extending across an opening of the petri dish, and a tube coupled to the planar portion, the tube oriented at an angle relative to the planar portion and defining a bore, the bore configured to receive a photoacoustic transducer for real-time multi-modal imaging of a sample within the petri dish.

In still another embodiment, the disclosure provides an adapter for a petri dish. The petri dish includes a bottom wall, a rim, a sidewall positioned between the bottom wall and the rim, and an opening defined by the rim. The adapter comprises a support portion including a first side and a second side, and a channel formed within the support portion and extending at least partially between the first side and the second side, the channel including a first surface, a second surface opposite the first surface, and an intermediate surface positioned between the first surface and the second surface, the channel configured to receive the rim of the petri dish such that the intermediate surface of the channel is positioned adjacent a top surface of the rim and the first surface and the second surface extend along opposite sides of the rim. The adapter also includes a tube coupled to the support portion and oriented at an angle relative to the support portion, the tube defining a bore configured to receive a photoacoustic transducer, and a guide member extending from the tube, the guide member configured to align the photoacoustic transducer and an optical microscope to an imaging region of a sample in the petri dish for real-time photoacoustic microscopy imaging.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Terms of degree, such as "substantially," "about," "approximately," etc. are understood by those of ordinary skill to refer to reasonable ranges outside of the given value, for example, general tolerances associated with manufacturing, assembly, and use of the described aspects.

For the specification of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Figure 1:
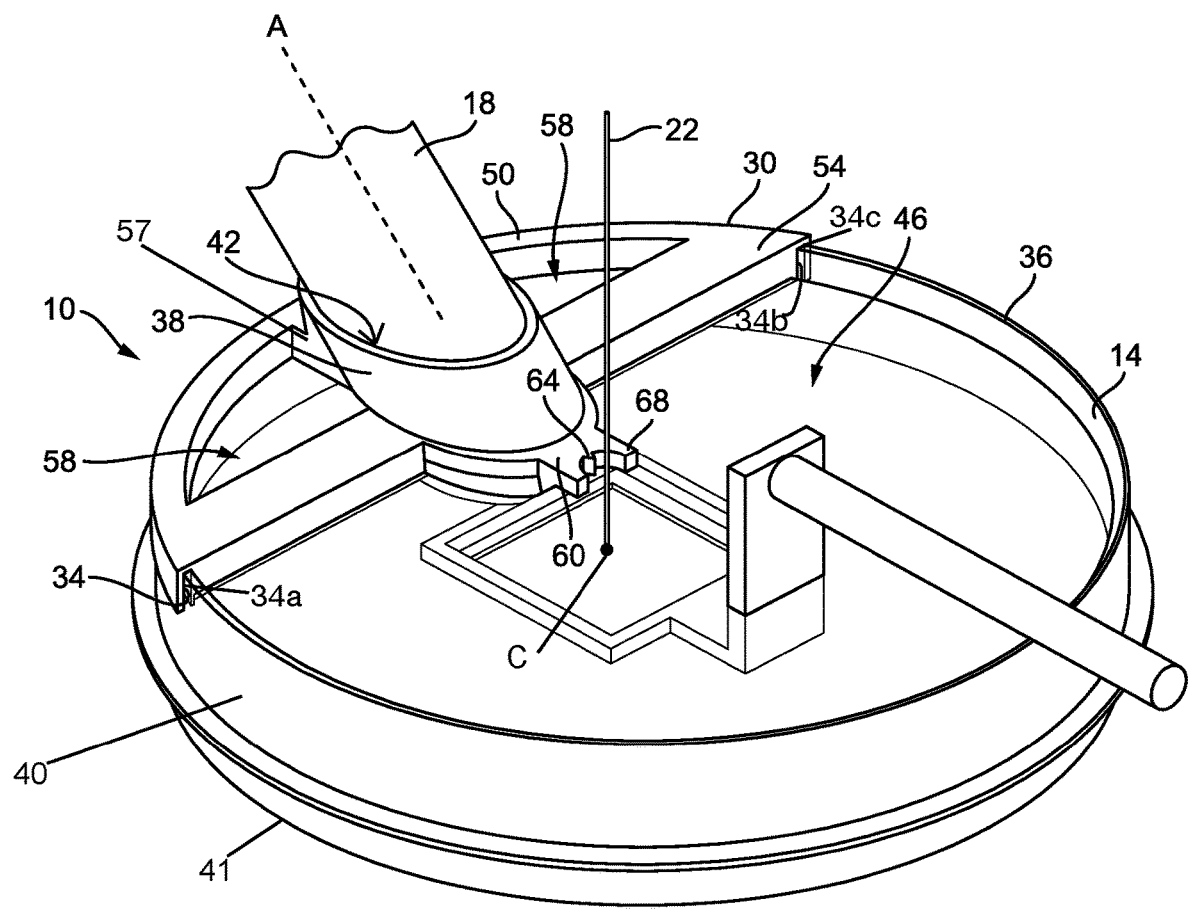
FIG. 1 illustrates a perspective view of an adapter for a container with a transducer positioned therein.
Figure 2:
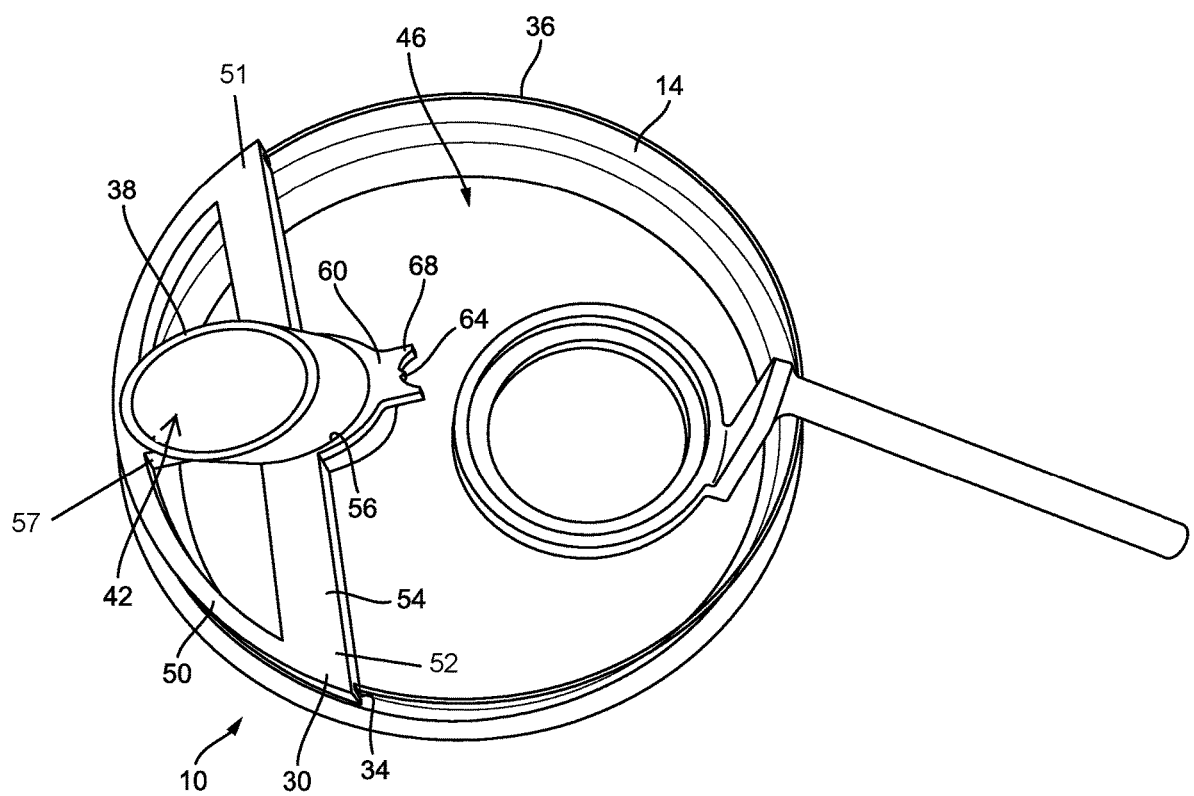
FIG. 2 illustrates another perspective view of an adapter for a container without a transducer positioned therein.
Figure 3:
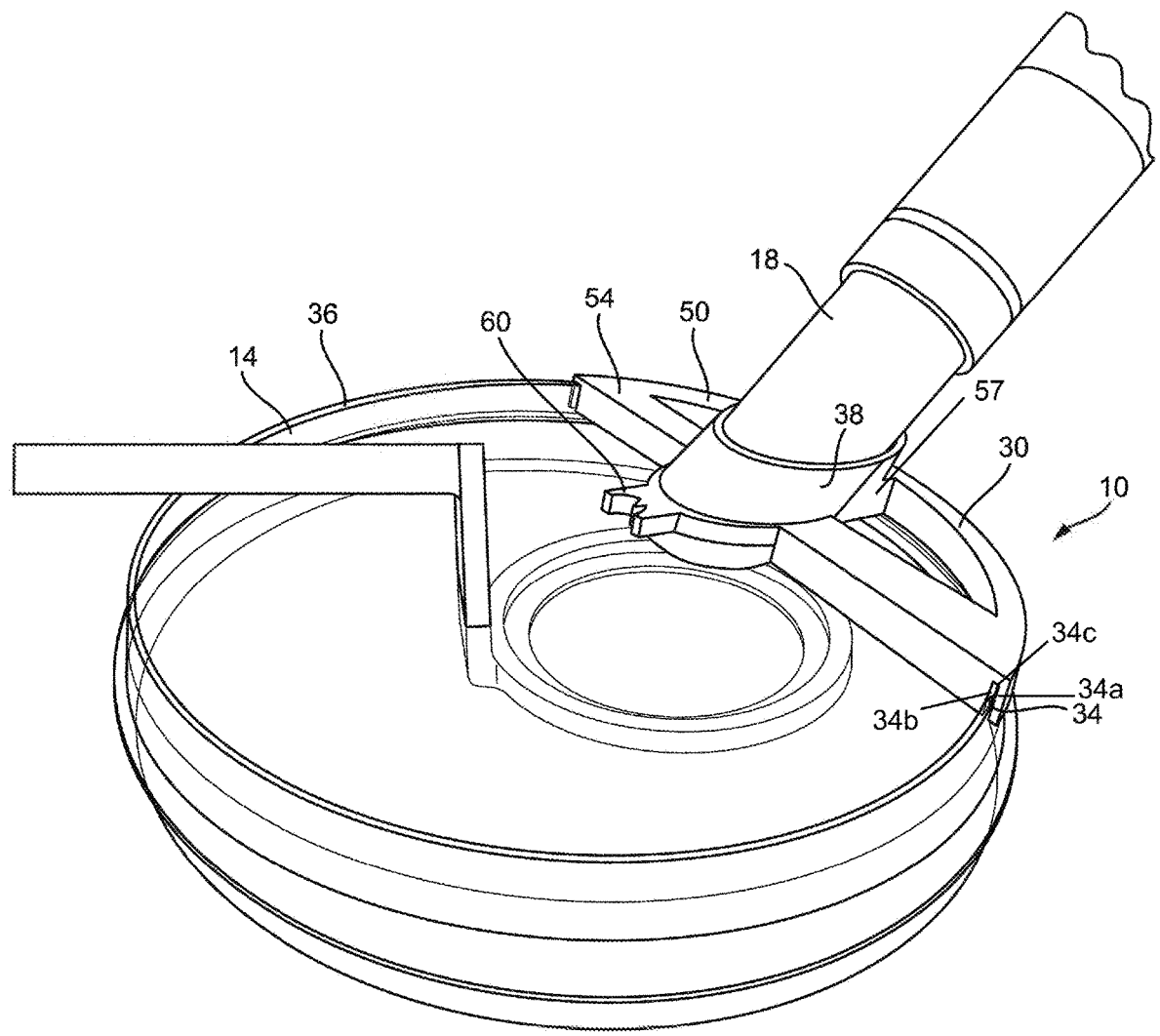
FIG. 3 illustrates another perspective view of an adapter for a container with a transducer positioned therein.

FIGS. 1-3 illustrate an adapter 10 that is removably positionable on and supported by a container 14. The adapter 10 is configured to fit securely on a portion of the container 14 for support above a sample in the container 14. The adapter 10 supports the angular placement and alignment of a transducer 18 relative to other imaging tools, such as an optical fiber 22 or an optical microscope. The adapter 10 can accommodate transducers having various sizes and dimensions. The adapter 10 provides a tool for multiple imaging modalities to simultaneously visualize a sample in the container. For example, the adapter 10 allows for overlapping foci or imaging region of an optical microscope and a photoacoustic transducer such that both imaging tools image or visualize the same or substantially the same portion of the sample in the container 14. Moreover, because the adapter 10 is configured to be supported on a container 14, it provides a photoacoustic microscopy system that is capable of real-time imaging of a sample within the container 14.

The container 14 includes a bottom wall 41 and a sidewall 40 extending from the bottom wall 41. The sidewall defines a rim 36. In the illustrated embodiment, the bottom wall 41 and the sidewalls are substantially circular, and the bottom wall 41 defines an imaging surface that is surrounded by the sidewall 40. In other embodiments, the container 14 may have any suitable shape. For example, the container 14 may include bottom walls and sidewalls that are rectangular, square, or polygonal. Additionally, the container 14 may be any suitable size.

The container 14 may include, for example, a petri dish or other surface culture dish. For example, a petri dish may be a 35 mm petri dish, a 60 mm petri dish, a 100 mm petri dish. The surface culture dish may be a flat bottom cell culture plate. The flat bottom cell culture plate may have 1 well, 6 wells, 12 wells, 24 wells, 48 wells, 96 wells, 384 wells, or any other number of wells.

With continued reference to FIGS. 1-3, the adapter 10 includes a base 30. As shown, in FIG. 1, the base 30 includes a support portion 50 and a planar portion 54. The support portion 50 includes a first end 51 and a second end 52. The support portion 50 also includes a channel 34 configured to receive the rim 36 of the container 14. The channel 34 may extend fully or partially between the first end 51 and the second end 52 of the support portion 50. The channel 34 includes a first surface 34a, a second surface 34b that is opposite the first surface 34a, and a top or intermediate surface 34c extending between the first and second surfaces 34a, 34b. When the adapter 10 is supported by the container 14 and the rim 36 is received in the channel 34, the first surface 34a is configured to be positioned adjacent a first or exterior surface of the sidewall 40, the second surface 34b is configured to be positioned adjacent a second or interior surface of the sidewall 40, and the intermediate surface 34c is positioned adjacent a top surface of the rim 36. In the illustrated embodiment, the support portion 50 is arcuately-shaped to be concentric with the sidewall 40 and rim 36 of the container 14. Similarly, the channel 34 is formed within and concentric with the support portion 50 to receive the rim 36 of the container 14.

The planar portion 54 extends between the first end 51 and the second end 52 of the support portion 50. That is, the planar portion 54 is formed with (or otherwise coupled to) and extends between opposite ends 51, 52 of the support portion 50. In this configuration, the planar portion 54 extends over an opening 46 of the container 14 and defines a plane that is oriented parallel to a plane defined by the rim 36 of the container 14 when the base 30 is coupled to the container 14. The planar portion 54 extends across the opening 46 but does not cross a center point C of the container 14. As illustrated, for example, in FIG. 1, the base 30 is positioned on a container 14, and the planar portion 54 does not cross over the center point C of the container 14.

The base 30 also includes a tube 38 that is oriented relative to the base 30 at an angle. In one construction, as illustrated, the tube 38 is connected to the planar portion 54 of the base 30. The tube 38 defines a bore 42 extending therethrough. The bore 42 continues through the planar portion 54 to accommodate a viewing range of the transducer 18 received within the tube 38.

The bore 42 defines an axis A that is oriented at an angle relative to the planar portion 54. The bore 42 includes a diameter, and in some embodiments, the diameter of the bore 42 may decrease from a first end of the tube 38 to a second end of the tube 38 (e.g., the first end of the tube 38 being further from the sample while the second end of the tube 38 being closer to the sample). In other embodiments, the diameter may remain constant along the length of the tube 38. The bore 42 is configured to receive the photoacoustic transducer 18 for real-time imaging of a sample within the container 14.

With reference to FIGS. 2-3, the planar portion 54 includes an aperture 56 that receives the tube 38, such that a portion of the tube 38 is positioned on both sides (e.g., a top side and a bottom side) of the planar portion 54. In some embodiments, a distal end of an immersion transducer 18 extends past the second end of the tube 38 such that it may be positioned in the container 14 (e.g., submerged within a fluid contained in the container 14). In some embodiments, a dry contact transducer 18 may be used. In such a case, the dry transducer 18 may be positioned above or adjacent to the sample and not submerged in the fluid.

The base 30 further includes a guide member 60. The guide member 60 may be integrally formed with or otherwise coupled to the base 30. In one construction, the guide member 60 is formed with (or otherwise coupled to) the planar portion 54. The guide member 60 extends from the planar portion 54 and toward the center point C of the container 14. As illustrated, the guide member extends forward of the tube 38 and is oriented parallel to the plane of the base 30. In other embodiments, the guide member 60 may be formed with the tube 68 and extend from the tube 68 toward the center point C of the container 14. As shown, the guide member 60 and the support portion 50 of the base 30 are positioned on opposite sides of the tube 38.

The guide member 60 includes an arcuately-shaped wall 68, and a projection 64 extending from the arcuately-shaped wall 64. The projection 64 is positioned centrally within the arcuately-shaped wall 64. The guide member 60 and the projection 64 are configured to assist with alignment of the photoacoustic transducer 18 relative to another imaging modality, such as an optical fiber 22 or an objective of a microscope for concurrent imaging or visualization of the sample in the container 14.

As discussed above, the planar portion 54 includes an aperture 56. The aperture 56 is formed in the planar portion 54 and can extend partially into the guide member 60. The tube 38 may be positioned such that it is positioned on the planar portion 54 and the guide member 60. The tube 38 may be coupled to the base 30, and specifically the planar portion 54, by any suitable means. For example, the tube 38 may be coupled to the base 30, and specifically the planar portion 54 by fasteners, adhesive, a friction fit engagement, or a snap-fit engagement. In other embodiments, the tube 38 may be integrally formed (e.g., formed as one-piece) with the base 30, and specifically the planar portion 54 (and, in some embodiments also the guide member 60).

As illustrated, the base 30 is coupleable to a portion of a perimeter of the rim 36 of the container 14. That is, the support portion 50 does not extend around or along the entire rim 36 of the container 14 when coupled thereto. In other constructions, the base 30 can extend around or along the entire rim 36 of the container 14 when coupled thereto.

In some embodiments, the base 30 can include a cross-bar 57 that is coupled between the planar portion 54 and the support portion 50 to provide extra support for the tube 38 and added weight of the transducer 18. The cross-bar 57 may also be coupled to the tube 38. For example, as illustrated in the figures, the cross-bar 57 extends perpendicularly from the planar portion 54 and tube 38, and couples to the support portion 50. The tube 38 extends from the planar portion 54 and the cross-bar 57. In some embodiments, the planar portion 54 or cross-bar 57 may at least partially define the aperture 56. In some embodiments, the planar portion 54 or the cross-bar 57 may at least partially define the bore 42. That is, the planar portion 54 or cross-bar 57 may define at least a portion of the tube 38.

With reference to FIG. 1, the cross-bar 57 divides an opening 58 between the support portion 50 and the planar portion 54 to provide two openings 58. In other embodiments, the opening 58 may be absent, and in such configuration, the planar portion 54 extends to the support portion 50. In some embodiments, there may be several cross-bars 57 extending between the planar portion 54 and the support portion 50. In an example including several cross-bars, several openings 58 (e.g., two, three, or four, etc.) may be formed in the base 30.

In the illustrated embodiment shown in FIGS. 1-3, the tube 38 is oriented at an angle relative to the base 30. As discussed above, the tube 38 defines the axis A, which is oriented at an angle relative to the base 30. In some embodiments, the angle may be between 10° and 90°. In other embodiments, the angle may be between 15° and 60°. The angle may be 10°, 15°, 20°, 25°, 30°, 35°, 40°, 45°, 50°, 55°, 60°, 65°, 70°, 75°, 80°, 85°, 90°, or any value between these values. The adapter 10 may be fixed in position on the rim 36 during use, but the adapter 10 may also be moveable around the rim 36 to reposition the tube 38 and the guide member 60 and therefore the transducer 18 and other imaging components, such as the optical fiber 22 or microscope objectives.

In other embodiments, the base 30 may be secured to a sidewall 40 of the container 14 or a bottom wall 41 of the container 14 or a combination of the rim 36, the sidewall 40, and the bottom wall 41. For example, the channel 34 may have a height that is sufficient to receive a portion of each of the rim 36, the sidewall 40, and the bottom wall 41 of the container 14. That is, in some embodiments, the channel 34 may include a first surface coupled to the planar portion 54, a second surface positioned opposite the first wall, and an intermediate surface positioned between the first surface and the second surface. With such a configuration, the first surface is positionable adjacent the rim 36, the second surface is positionable adjacent the bottom wall 41, and the intermediate surface is positionable adjacent the exterior surface of the container 14. The base 30 may rest on the rim of the container 14 or be removably coupled to the container 14 with a friction fit or snap-fit engagement or other type of engagement.

In other embodiments, the support portion 50 of the base 30 may have other shapes to correspond with the walls of the respective container 14, e.g., petri dish or surface culture dish. For example, the support portion 50 may have a single straight wall that receives a complementary wall of a petri dish or surface culture dish or a plurality of walls that are coupled to and oriented at perpendicular or other angles relative to one another to accommodate rectangular or square-shaped polygonal shaped petri dishes or surface culture dishes.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

Various features and advantages of the adapter are set forth in the following claims.

What is claimed is:

1. An adapter for a container, the container including a bottom wall, a rim, a sidewall positioned between the bottom wall and the rim, and an opening defined by the rim, the adapter comprising:
   a support portion including a channel formed therein, the channel including a first surface, a second surface spaced apart from the first surface, and an intermediate surface positioned between the first surface and the second surface, the channel configured to receive the rim of the container such that the intermediate surface of the channel is positioned adjacent a top surface of the rim and the first surface and the second surface extend along opposite sides of the sidewall;
   a planar portion formed with the support portion and configured to extend across the opening of the container at a non-central point relative to the opening of the container; and
   a tube coupled to and extending from the planar portion, the tube defining a bore having an axis, the axis being oriented at an angle relative to the planar portion, the bore configured to receive a photoacoustic transducer for real time imaging of a sample within the container.

2. The adapter of claim 1, wherein the angle is between 10° and 90°.

3. The adapter of claim 1, wherein the angle is between 15° and 60°.

4. The adapter of claim 1, wherein the container is circular, and further wherein the channel in the support portion is arcuately-shaped and is configured to receive an arcuate portion of the rim.

5. The adapter of claim 1, further comprising a cross-bar extending between the planar portion and the support portion.

6. The adapter of claim 1, further comprising a guide member extending from the planar portion, and wherein the guide member and the support portion are positioned on opposite sides of the tube, the guide member configured to position the photoacoustic transducer relative to an optical fiber or an objective of a microscope.

7. The adapter of claim 1, further comprising a guide member extending from the planar portion, the guide member including an arcuately-shaped wall with a projection extending from the arcuately shaped wall, the projection configured to position the photoacoustic transducer relative to an optical fiber or an objective of a microscope.

8. The adapter of claim 1, further comprising a guide member extending from the tube, the guide member including a projection configured to position the photoacoustic transducer relative to an optical fiber or an objective of a microscope.

9. An adapter for a petri dish, the petri dish including a bottom wall, a rim, a sidewall positioned between the bottom wall and the rim, and an opening defined by the rim, the adapter comprising:
   an arcuately-shaped support portion including a first end and a second end;
   a channel formed within the support portion and extending between the first end and the second end, the channel configured to receive the rim of the petri dish;
   a planar portion coupled to the support portion between the first end and the second end, the planar portion configured to extend at least partially over an opening of the petri dish; and
   a tube coupled to the planar portion, the tube oriented at an angle relative to the planar portion and defining a bore, the bore configured to receive a photoacoustic transducer for real-time multi-modal imaging of a sample within the petri dish.

10. The adapter of claim 9, further comprising a guide member extending from the planar portion or the tube, the support portion and the guide member positioned on opposite sides of the tube, the guide member configured to position the photoacoustic transducer relative to an optical fiber or an objective of a microscope.

11. The adapter of claim 9, wherein the angle is between 10° and 90°.

12. The adapter of claim 9, wherein the angle is between 15° and 60°.

13. An adapter for a petri dish, the petri dish including a bottom wall, a rim, a sidewall positioned between the bottom wall and the rim, and an opening defined by the rim, the adapter comprising:
   a support portion including a first end and a second end;
   a channel formed within the support portion and extending at least partially between the first end and the second end, the channel including a first surface, a second surface spaced apart from the first surface, and an intermediate surface positioned between the first surface and the second surface, the channel configured to receive the rim of the petri dish such that the intermediate surface of the channel is positioned adjacent a top surface of the rim and the first surface and the second surface extend along opposite sides of the rim;
   a tube coupled to the support portion and oriented at an angle relative to the support portion, the tube defining a bore configured to receive a photoacoustic transducer; and
   a guide member extending from the tube, the guide member configured to position the photoacoustic transducer and an optical microscope relative to an imaging region of a sample in the petri dish for real-time photoacoustic microscopy imaging.

14. The adapter of claim 13, wherein the angle is between 10° and 90°.

15. The adapter of claim 13, wherein the angle is between 15° and 60°.

16. The adapter of claim 13, further comprising a planar portion coupled to the support portion and extending between the first end and the second end.

17. The adapter of claim 16, further comprising a cross-bar coupled between the support portion and the tube.

18. The adapter of claim 17, wherein the tube is coupled to the planar portion, and wherein the planar portion includes an aperture for the photoacoustic transducer to image the sample.

* * * * *